United States Patent [19] [11] 4,428,881
Hedrich et al. [45] Jan. 31, 1984

[54] CONTROL OF UNWANTED VEGETATION WITH N-CARBAMYLINDOLINES

[75] Inventors: Loren W. Hedrich, Overland Park; Ralph P. Neighbors, Olathe, both of Kans.

[73] Assignee: Gulf Oil Corporation, Pittsburgh, Pa.

[21] Appl. No.: 864,042

[22] Filed: Dec. 23, 1977

[51] Int. Cl.³ .............................................. C07D 27/38
[52] U.S. Cl. ........................................ 548/491; 71/96
[58] Field of Search .................. 71/96; 860/326.11 R, 860/319.1

[56] References Cited

U.S. PATENT DOCUMENTS 3,890,348  6/1975  Kathawala ................ 260/326.11 R
4,080,330  3/1978  Kubela et al. .............. 260/326.11 R

OTHER PUBLICATIONS

Mazza et al., Il Farmaco. Ed. Sc., vol. 31, Fasc. 10 (1976), pp. 746–754.

Primary Examiner—Catherine L. Mills
Attorney, Agent, or Firm—Deane E. Keith; Forrest D. Stine

[57] ABSTRACT

New N-carbamylindolines which are useful in combating unwanted vegetation by both pre-emergent and post-emergent application are compounds having the structural formula

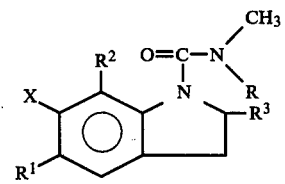

in which R and $R^3$ are hydrogen or methyl, $R^1$ is hydrogen or N,N-dimethylsulfamyl, N,N-diethylsulfamyl, N-methoxy-N-methyl-sulfamyl, bromo or chloro, X is hydrogen or fluoro and $R^2$ is hydrogen or dimethylsulfamyl, with the provision that at least one and no more than two substituents represented by $R^1$, $R^2$, and $R^3$ and X are present.

8 Claims, No Drawings

CONTROL OF UNWANTED VEGETATION WITH N-CARBAMYLINDOLINES

DESCRIPTION OF THE INVENTION

A. Background

The N-acylindolines as a class would not be expected to be phytotoxic. (See, for example, Hans Geissbuehler, Henry Martin and Guenther Voss in "Herbicides- Chemistry, Degradation, and mode of Action", 2nd Ed., P. C. Kearney and D. D. Kaufman, Eds., Marcell Dekker, New York, Vol. 1, 1975, chapter 3.) Although a few simple N-carbamylindolines do exhibit an interesting level of phytotoxicity, many are almost totally inactive and others have so little phytotoxicity that they have no substantial utility as herbicides. When an attempt is made to make phytotoxic N-carbamylindolines with ring substituents, the results are even more discouraging. For example, compounds having substituents as indicated below have no phytotoxic activity of practical value:

or post-emergently to effectively combat unwanted vegetation. The novel herbicides are compounds having the structural formula

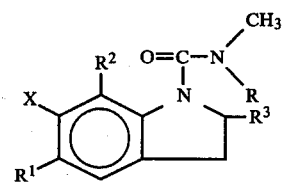

in which R and $R^3$ are hydrogen or methyl, $R^1$ is N, N-dimethylsulfamyl, N, N-diethylsulfamyl, N-methoxy-N-methylsulfamyl, bromo or chloro, X is hydrogen or fluoro and $R^2$ is hydrogen or dimethylsulfamyl, with the provision that at least one and no more than two substituents represented by $R^1$, $R^2$, $R^3$ and X are always present and are other than hydrogen.

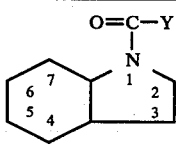

Compounds without ring substituents

| Y | m.p. ° C. |
|---|---|
| —NHC4H9 | 76–77 |
| —NHC(CH3)3 | 135–36 |
| —NHC6H13 | Oil |
| —NHC12H25 | 60–61 |
| —NHC18H37 | 77 |
| —NHCH2CH2Cl | 99 |
| —NHSO2Cl | 132–133 |
| —NH phenyl | 111.5–112.5 |
| —NH—(p-chlorophenyl) | 179–80 |
| —NH—(3,4-dichlorophenyl) | 145 |
| —NH—(3,6-dichlorophenyl) | 199.5–200 |
| —NH—(p-fluorophenyl) | 161.5–162.5 |
| —NH—(p-tolyl) | 130.5–131.5 |
| —NH—(o-tolyl) | 156.5–157 |
| —NH—(p-nitrophenyl) | 222–223.5 |
| —NH—(m-nitrophenyl) | 216.5–218 |
| —NH—(o-nitrophenyl) | 190–191 |

Compounds with Substituents at more than one position

| Y | Other Positions | m.p. °C. |
|---|---|---|
| —NH—CH2—CH=CH2 | 2-methyl | 100–102 |
| —NHCH3 | 5-nitro | 225–226 |
| —NHCH3 | 6-nitro | 245(dec.) |
| —NHCH3 | 6-amino | 151–152 |
| —NHCH3 | 6-(3-methylureido) | 220–222 |
| —NHCH3 | 5-acetyl | 158–161 |
| —NHCH3 | 5-chlorosulfonyl | 140–145 |
| —NHCH3 | 5-sulfamyl | 240–241 |
| —NHCH3 | 5-(N—methylsulfamyl) | 244–246 |
| —NHCH3 | 5-bromo-7-(N—methoxy-N—methylsulfamyl) | 197–198 |
| —NHCH3 | 5-bromo-7-(N,N—diethylsulfamyl) | 195–197 |
| —NHCH3 | 5,6-dinitro | 177–180 |
| —N(CH3)2 | 5-amino | oil |
| —NHCH3 | 5,6-diamino | 182–185 |
| —NH(CH3)2 | 5-chlorosulfonyl | 117–118 |
| —NH(CH3)2 | 5-sulfamyl | 263–264 |
| —N(CH3)2 | 5-bromo-7-nitro | oil |
| —N(CH3)2 | 5-bromo-7-(N—methylsulfamyl) | 180–181 |
| —N(CH3)2 | 5-bromo-(N,N—diallylsulfamyl) | 79–81 |

B. SUMMARY

We have discovered that a limited class of ringsubstituted 1-carbamylindolines may be applied, either pre

C. DETAILED DESCRIPTION

Below are listed specific compounds of the above structural formula which are illustrative of the class herbicides of the present invention.

| No. | R | $R^1$ | $R^2$ | $R^3$ | X | m.p. °C. |
|---|---|---|---|---|---|---|
| 1 | H | H | H | $CH_3$ | H | 153–5 |
| 2 | H | Cl | H | H | H | 182–4 |
| 3 | H | $(CH_3)_2NSO_2$ | H | H | H | 176–8 |
| 4 | H | Br | H | H | H | 199–201 |
| 5 | $CH_3$ | H | H | H | F | 78–80 |
| 6 | H | H | H | H | F | 193–4 |
| 7 | H | $(C_2H_5)_2NSO_2$ | H | H | H | 152–3 |
| 8 | H | $CH_3(CH_3O)NSO_2$ | H | H | H | 152–152.5 |
| 9 | $CH_3$ | Br | $(CH_3)_2NSO_2$ | H | H | oil |
| 10 | H | Br | $(CH_3)_2NSO_2$ | H | H | 174–5 |
| 11 | H | Cl | H | $CH_3$ | H | 142–4 |
| 12 | $CH_3$ | Cl | H | $CH_3$ | H | oil |
| 13 | $CH_3$ | Cl | H | H | H | oil |
| 14 | $CH_3$ | Br | H | H | H | oil |
| 15 | $CH_3$ | $(CH_3)_2NSO_2$ | H | H | H | 119–120 |
| 16 | $CH_3$ | $(C_2H_5)_2NSO_2$ | H | H | H | 93–5 |
| 17 | $CH_3$ | $CH_3(CH_3O)NSO_2$ | H | H | H | 112–113 |

(1) PREPARATION OF THE HERBICIDES

The methods of preparation outlined below are typical of those employed to make the compounds listed above.

PREPARATION OF 5-CHLOROSULFONYL-N-METHYLINDOLINE-1-CARBOXAMIDE

To 450 g of stirred and ice-bath cooled chlorosulfonic acid was added N-methylindoline-1-carboxamide (135 g, 0.77 mol) portion wise and at such a rate that the temperature did not exceed 20°–25° C. On completion of the addition, the ice-bath was removed and the solution was heated to 60° for two hours. After pouring onto 500 ml of ice water the mixture was extracted with three 100 ml portions of chloroform. The combined extracts were washed once with saturated sodium chloride solution and dried 30 minutes over anhydrous magnesium sulfate. Distillation of the solvent afforded 98 g of tacky product which solidified on being stirred in benzene with a few ml of acetone, m.p. 140°–5° C. The product was used without further purification. Infrared spectrum, nuclear magnetic resonance spectrum and elemental analysis were consistent with the desired product.

PREPARATION OF 5-(N-METHOXY-N-METHYL-SULFAMYL)-N-METHYLINDOLINE-1-CARBOXAMIDE

A mixture of 10 ml of water and 30 ml of acetone was cooled below 10° C. Potassium acetate (4.9 g) was dissolved followed by 3.5 g (35 mmol) of N, O-dimethylhydroxylamine hydrochloride added portion wise and stirred for ½ hr. A suspension of 5-chlorosulfonyl-N-methylindoline-1-carboxamide (9.7 g, 35 mmol) in 100 ml of acetone was added dropwise and stirred overnight, after which a homogeneous solution resulted. The solvent was distilled and the product was crystallized from ethanol-water, m.p. 152.0°–152.5° C. The infrared spectrum, nuclear magnetic resonance spectrum and elemental analysis were all in agreement with the desired product.

PREPARATION OF N-METHOXY-N-METHYLINDOLINE-1-CARBOXAMIDE

A solution of indoline (5.4 g, 45 mmol), 5.4 ml of triethylamine and N-methoxy-N-methylcarbamoyl chloride (4.2 g, 45 mmol) in 100 ml of dry benzene was refluxed for 48 hrs. The solution was cooled and washed with 10% HCl and saturated sodium chloride solution. The organic layer was dried over anhydrous magnesium sulfate. The solvent was distilled affording a brown liquid which distilled at 129°/0.5 mm. Infrared spectrum, nuclear magnetic resonance spectrum and analysis were consistent with the desired product.

(2) COMBATING UNWANTED VEGETATION

The novel herbicides are effective when used both post- and pre-emergently. In commercial use the compounds are formulated as herbicidal compositions in combination with an inert diluent and a surface active agent. There is described below an illustrative procedure for herbicidal use of the compounds under controlled conditions in the greenhouse so as to obtain data on phytotoxic activity and selectivity.

POST EMERGENT USE

An aqueous dispersion of each active compound is prepared by combining 0.4 gram of the compound with about 4 ml of a solvent-emulsifier mixture (3 parts of a commercial polyoxyethylated vegetable oil emulsifier, 1 part xylene, 1 part kerosene) and then adding water, with stirring, to a final volume of 40 ml.

The species of plants on which each compound is to be tested are planted in 4-inch pots in a greenhouse. Ten to 18 days after emergence of the plants, three pots of each species are sprayed with an aqueous dispersion of the active compound prepared as described above, at the indicated rate of active compound per acre and at a spray volume of 60 gallons per acre. Approximately 2 weeks after the spray application the plants are observed and the results rated according to the following schedule:

DEGREE OF EFFECT

0 = no effect
1 = slight effect (temporary injury)
2 = moderate effect (some permanent injury)
3 = severe effect (some plants died)
4 = maximum effect (all plants died)

The same rating schedule is employed to judge pre-emergent results obtained according to the procedure below.

PRE-EMERGENT USE

A solution of each active compound is prepared by dissolving 290 mg of the compound to be tested in 200 ml of acetone. Disposable expanded polystyrene trays about 2½ inches deep and about 1 square foot in area are prepared and sprayed with the acetone solution at the indicated rate of active chemical per acre of sprayed area and are then covered with about one-fourth inch of soil. Twenty-one days after seeding and treatment the plants are examined and herbicidal effects are rated according to the above schedule.

Both post-emergent and pre-emergent results which have been obtained with the herbicides are set forth in the following tables.

| PLANT SPECIES | Appl'n. Rate (lb./A.) | 1 POST | 1 PRE | 2 POST | 2 PRE | 4 POST | 4 PRE | 5 POST | 5 PRE | 6 POST | 6 PRE | 11 POST | 11 PRE | 3 POST | 3 PRE | 7 POST | 7 PRE | 8 POST | 8 PRE | 9 POST | 9 PRE | 10 POST | 10 PRE | 12 POST | 12 PRE | 13 POST | 13 PRE | 14 POST | 14 PRE | 15 POST | 15 PRE | 16 POST | 16 PRE | 17 POST | 17 PRE |
|---|---|---|---|---|---|---|---|---|---|---|---|---|---|---|---|---|---|---|---|---|---|---|---|---|---|---|---|---|---|---|---|---|---|---|---|
| *Celosia plumosa* Coxcomb | 5 | 4 | | 4 | | 3 | 1 | | 4 | | 4 | 4 | 4 | | | | | | | | | | | | | | | | | | | | | | |
| | 3 | 4 | 3 | 4 | 2 | 1 | 0 | 2 | 0 | 4 | 3 | 4 | 3 | | | | | | | | | | | | | | | | | | | | | | |
| *Setaria italica* Millet | 5 | 4 | 3 | 4 | 4 | 4 | 4 | 2 | 4 | 4 | 3 | 4 | 4 | | | | | | | | | | | | | | | | | | | | | | |
| | 3 | 3 | 2 | 4 | 4 | 4 | 4 | 4 | 2 | 4 | 3 | 4 | 4 | | | | | | | | | | | | | | | | | | | | | | |
| *Arena sativa* Oats | 5 | 0 | 2 | 4 | 4 | 4 | 4 | 0 | 1 | | | 4 | 4 | | | | | | | | | | | | | | | | | | | | | | |
| | 3 | 3 | | 4 | 1 | 1 | 0 | 0 | 0 | 3 | 2 | 3 | 0 | | | | | | | | | | | | | | | | | | | | | | |
| *Linum usitatissimum* Flax | 5 | 0 | 3 | 4 | 4 | 4 | 4 | 0 | 3 | 4 | | 4 | 4 | | | | | | | | | | | | | | | | | | | | | | |
| | 3 | 3 | 0 | 4 | 4 | 4 | 4 | 2 | 1 | 4 | 2 | 4 | 4 | | | | | | | | | | | | | | | | | | | | | | |
| *Raphanus sativus* Radish | 5 | 0 | 1 | 4 | 4 | 4 | 4 | 0 | 1 | | | 4 | 4 | | | | | | | | | | | | | | | | | | | | | | |
| | 3 | 0 | | 3 | 2 | 4 | 1 | 3 | 0 | 4 | 4 | 4 | 2 | | | | | | | | | | | | | | | | | | | | | | |
| *Xanthium pensylvanicum* Cockelbur | 3 | | | | | | | | | | | | | 0 | 1 | 0 | 0 | 2 | 0 | 0 | 0 | 0 | 0 | 2 | 1 | 3 | 0 | 1 | 0 | | | | | 2 | 3 |
| | 1 | | | | | | | | | | | | | 0 | 1 | 0 | 0 | 0 | 4 | 3 | 1 | 0 | 1 | 1 | 1 | 4 | 0 | 0 | 4 | 3 | 1 | 2 | 1 | 4 | 1 |
| *Chenopodium album* Lambsquarters | 3 | | | | | | | | | | | | | 4 | 3 | 4 | 3 | 4 | 2 | 4 | 2 | 1 | 0 | 4 | 4 | 4 | 4 | 4 | 4 | 4 | 3 | 4 | 1 | 4 | 3 |
| | 1 | | | | | | | | | | | | | 0 | 2 | 1 | 2 | 4 | 2 | 1 | 0 | 1 | 0 | 4 | 3 | 4 | 0 | 4 | 2 | 3 | 0 | 4 | 0 | 4 | 2 |
| *Ipomoea purpurea* Morning Glory | 3 | | | | | | 3 | | | 1 | 0 | 3 | 1 | 0 | 0 | 2 | 0 | 4 | 2 | 1 | 0 | 2 | 0 | 4 | 3 | 4 | 0 | 4 | 4 | 4 | 2 | 4 | 2 | 4 | 3 |
| | 1 | | | | | | 1 | 1 | | | | | | 0 | 1 | 0 | 0 | 4 | 1 | 0 | 0 | 2 | 0 | 4 | 1 | 2 | 0 | 2 | 4 | 2 | 0 | 2 | 0 | 4 | 1 |
| *Amaranthus retroflexus* Pigweed | 3 | | | | | | | | | 2 | 0 | 3 | 0 | 0 | 1 | 4 | 0 | 4 | 4 | 2 | 0 | 4 | 3 | 4 | 4 | 4 | 4 | 4 | 4 | 4 | 0 | 4 | 2 | 4 | 4 |
| | 1 | | | | | | 1 | 3 | | | | | | 0 | 0 | 4 | 3 | 2 | 0 | 0 | 0 | 3 | 0 | 3 | 3 | 4 | 1 | 4 | 2 | 4 | 3 | 4 | 2 | 4 | 4 |
| *Polygonum convolvulus* Wild Buckwheat | 3 | | | | | | 0 | | | 2 | 0 | 4 | 4 | 0 | 0 | 3 | 0 | 4 | 4 | 4 | 4 | 3 | 1 | 4 | 3 | 4 | 4 | 4 | 1 | 4 | 0 | 4 | 4 | 4 | 1 |
| *Brassica kaber* Wild Mustard | 5 | 4 | 4 | 4 | 4 | 4 | 4 | | | 4 | 4 | 4 | 4 | 1 | 0 | 3 | 1 | 4 | 4 | 2 | 0 | 3 | 1 | 4 | 4 | 4 | 4 | 4 | 4 | 2 | 4 | 4 | 2 | 4 | 4 |
| | 3 | 4 | 4 | 3 | 1 | 2 | 2 | 3 | 0 | 4 | 4 | 2 | 2 | 0 | 0 | 1 | 0 | 3 | 3 | 3 | 2 | 1 | 0 | 3 | 2 | 4 | 4 | 4 | 2 | 4 | 4 | 4 | 2 | 4 | 2 |
| *Echinochloa crusgalli* Barnyard grass | 5 | | | 3 | 1 | 3 | 1 | | | 1 | 0 | 3 | 1 | 0 | 0 | 1 | 0 | 2 | 1 | 3 | 2 | 3 | 1 | 3 | 1 | 2 | 0 | 3 | 0 | 3 | 1 | 0 | 0 | 0 | 0 |
| | 3 | | | | | 2 | 1 | | | 2 | 0 | 4 | 1 | 0 | 0 | 2 | 0 | 2 | 0 | 0 | 0 | 0 | 0 | 1 | 0 | 4 | 1 | 4 | 1 | 1 | 0 | 0 | 0 | 1 | 0 |
| *Digitaria sanguinalis* Crabgrass | 5 | 3 | | 4 | 1 | 4 | 3 | | | | 3 | 4 | 1 | 1 | 0 | 2 | 0 | 2 | 0 | 2 | 1 | 2 | 0 | 4 | 0 | 4 | 1 | 3 | 1 | 4 | 0 | 0 | 0 | 1 | 0 |
| | 3 | | | | | 1 | 1 | | | | | 3 | 1 | 1 | 0 | 0 | 0 | 2 | 0 | 1 | 0 | 1 | 0 | 2 | 0 | 3 | 0 | 3 | 0 | 2 | 0 | 0 | 0 | 1 | 0 |
| *Bromus tectorum* Downy Brome | 5 | 4 | | 3 | | 2 | 1 | | | 2 | 0 | 3 | 1 | 1 | 0 | 1 | 0 | 1 | 0 | 1 | 0 | 1 | 0 | 2 | 0 | 2 | 0 | 3 | 0 | 1 | 0 | 0 | 0 | 1 | 0 |
| | 3 | 0 | | 0 | 1 | 1 | 0 | 0 | 0 | 2 | 0 | 3 | 1 | 0 | 0 | 0 | 0 | 1 | 0 | 0 | 0 | 0 | 0 | 2 | 0 | 2 | 0 | 2 | 0 | 2 | 0 | 0 | 0 | 2 | 0 |
| *Setaria faberii* Giant Foxtail | 5 | 0 | 0 | 2 | 2 | 2 | 3 | | | 1 | 0 | 3 | 0 | 0 | 0 | 0 | 0 | 3 | 0 | 0 | 0 | 2 | 0 | 3 | 0 | 3 | 1 | 4 | 3 | 2 | 0 | 0 | 0 | 2 | 0 |
| | 3 | 0 | | 0 | 0 | 2 | 1 | | | 4 | 0 | 4 | 2 | 0 | 0 | 1 | 0 | 3 | 0 | 0 | 0 | 3 | 1 | 4 | 3 | 4 | 1 | 4 | 3 | 4 | 0 | 2 | 0 | 0 | 0 |
| *Setaria viridis* Green Foxtail | 5 | 1 | 0 | 3 | 1 | 4 | 2 | | | 4 | 0 | 4 | 4 | 0 | 1 | 0 | 1 | 3 | 0 | 0 | 0 | 3 | 1 | 4 | 1 | 3 | 3 | 4 | 1 | 2 | 0 | 2 | 0 | 2 | 1 |
| *Cyperus esculentis* Nutsedge | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

-continued

| PLANT SPECIES | Appl'n. Rate (lb./A.) | 1 PRE | 1 POST | 2 PRE | 2 POST | 4 PRE | 4 POST | 5 PRE | 5 POST | 6 PRE | 6 POST | 11 PRE | 11 POST | 3 PRE | 3 POST | 7 PRE | 7 POST | 8 PRE | 8 POST | 9 PRE | 9 POST | 10 PRE | 10 POST | 12 PRE | 12 POST | 13 PRE | 13 POST | 14 PRE | 14 POST | 15 PRE | 15 POST | 16 PRE | 16 POST | 17 PRE | 17 POST |
|---|---|---|---|---|---|---|---|---|---|---|---|---|---|---|---|---|---|---|---|---|---|---|---|---|---|---|---|---|---|---|---|---|---|---|---|
| Sorghum bicolor Shatter Cane | 5 3 | 0 0 | 0 0 | 3 0 | 4 2 | 2 0 | 2 4 | 0 0 | 0 0 | 1 0 | 1 0 | 2 1 | 4 2 | 0 0 | 0 0 | 0 0 | 2 1 | 2 0 | 1 0 | 0 0 | 1 1 | 1 0 | 0 0 | 2 0 | 2 0 | 2 0 | 3 1 | 1 0 | 3 1 | 0 0 | 1 0 | 0 0 | 0 0 | 1 0 | 1 0 |
| Avena fatua Wild Oats | 5 3 1 | 3 0 | 3 0 | 2 0 | 3 1 | 0 0 | 1 0 | 0 0 | 0 0 | 3 1 | 3 1 | 1 0 | 1 0 | 0 0 | 0 0 | 0 0 | 3 1 | 4 0 | 2 0 | 1 0 | 1 0 | 0 0 | 0 0 | 3 1 | 3 0 | 3 0 | 1 0 | 0 0 | 2 0 | 2 0 | 1 0 | 1 0 | 1 0 | 1 0 | 1 0 |
| Medicago sativa Alfalfa | 5 3 1 | 4 1 4 | 4 3 1 | 4 3 | 4 4 | 4 2 | 4 1 | 3 0 2 | 1 0 0 | 3 1 | 3 2 | 4 2 | 4 3 | 0 0 | 4 3 | 2 0 | 2 3 | 4 0 | 4 2 | 4 2 | 4 2 | 2 1 | 4 2 | 4 2 | 4 2 | 4 0 | 4 2 | 4 2 | 4 0 | 4 1 | 4 3 | 3 1 | 2 1 | 4 1 | 4 2 |
| Gossypium herbaceum Cotton | 5 3 1 | 3 0 0 | 1 0 0 | 1 0 | 3 0 | 0 0 | 4 1 | 0 0 | 3 0 | 3 0 | 2 0 | 0 0 | 4 4 | 0 0 | 4 3 | 0 0 | 3 1 | 0 0 | 4 3 | 0 0 | 4 4 | 0 0 | 4 4 | 3 2 | 4 2 | 4 0 | 4 1 | 2 1 | 2 1 | 0 0 | 4 4 | 4 1 | 4 0 | 4 2 | 4 2 |
| Arachis hypogaea Peanut | 5 3 1 | 3 | 0 0 | 0 1 | 2 1 | 0 0 | 0 0 | 1 0 | 1 0 | 2 0 | 2 0 | 0 0 | 0 1 | 0 0 | 0 0 | 0 0 | 0 0 | 0 0 | 1 0 | 1 0 | 1 0 | 0 0 | 1 0 | 1 0 | 1 0 | 0 0 | 1 0 | 0 0 | 1 0 | 0 0 | 1 1 | 0 0 | 1 0 | 0 0 | 1 0 |
| Soja max Soybean | 5 3 1 | 2 1 1 | 2 1 1 | 3 1 | 4 3 | 0 0 | 0 1 | 1 0 0 | 1 0 1 | 2 1 | 2 1 | 3 0 | 4 2 | 0 0 | 3 3 | 1 0 | 4 1 | 3 1 | 4 3 | 0 0 | 3 1 | 0 0 | 2 1 | 3 1 | 3 2 | 1 0 | 3 2 | 0 0 | 1 1 | 4 1 | 3 2 | 3 3 | 3 2 | 4 3 | 4 3 |
| Beta vulgaris Sugar Beets | 5 3 1 | 4 1 4 | 4 3 | 4 3 | 4 4 | 4 4 | 4 2 | 3 1 4 | 3 1 | 4 3 | 4 3 | 4 4 | 4 4 | 0 0 | 3 3 | 0 0 | 4 1 | 4 1 | 4 3 | 0 0 | 4 4 | 1 0 | 4 4 | 4 2 | 4 2 | 4 4 | 4 1 | 4 2 | 4 2 | 3 0 | 3 4 | 3 2 | 3 2 | 4 2 | 4 3 |
| Lycopersicum esculentum Tomato | 5 3 1 | 4 3 | 4 1 | 4 1 | 4 4 | 4 1 | 4 4 | 3 1 | 3 1 | 4 3 | 4 3 | 4 1 | 4 4 | 1 0 | 4 3 | 0 0 | 4 1 | 4 0 | 4 3 | 0 0 | 4 3 | 0 0 | 4 4 | 4 3 | 4 3 | 4 1 | 4 3 | 4 1 | 4 3 | 4 1 | 4 4 | 4 3 | 4 3 | 4 3 | 4 3 |
| Zea mays Corn | 5 3 1 | 1 0 | 0 0 | 2 0 | 2 1 | 0 0 | 0 1 | 0 0 | 0 0 | 0 0 | 0 0 | 0 1 | 2 1 | 0 0 | 0 0 | 0 0 | 0 0 | 1 0 | 1 0 | 0 0 | 1 0 | 0 0 | 0 0 | 1 0 | 1 0 | 3 0 | 1 0 | 1 0 | 3 0 | 0 0 | 1 0 | 1 0 | 1 0 | 1 0 | 1 0 |
| Sorghum vulgare Grain Sorghum | 5 3 1 | 0 0 | 0 0 | 2 0 | 4 2 | 0 0 | 4 0 | 0 0 | 0 0 | 0 0 | 0 0 | 2 0 | 4 1 | 0 0 | 0 0 | 0 0 | 1 0 | 1 0 | 1 0 | 0 0 | 1 1 | 0 0 | 0 0 | 1 0 | 1 0 | 2 0 | 2 1 | 0 0 | 3 0 | 0 0 | 1 0 | 0 0 | 0 0 | 0 0 | 1 0 |
| Oryza sativa Rice | 5 3 1 | 0 0 | 0 0 | 3 0 | 3 0 | 0 0 | 4 1 | 0 0 | 0 0 | 1 0 | 1 0 | 2 0 | 2 0 | 0 0 | 0 0 | 0 0 | 3 1 | 3 1 | 2 0 | 0 0 | 1 1 | 0 0 | 1 0 | 1 0 | 1 0 | 3 0 | 3 0 | 0 0 | 4 1 | 0 0 | 1 0 | 0 0 | 0 0 | 1 0 | 1 0 |
| Triticum aestivum Wheat | 5 3 1 | 1 0 | 3 0 | 3 0 | 4 2 | 0 0 | 2 0 | 0 0 | 0 0 | 2 0 | 2 0 | 1 0 | 2 0 | 0 0 | 0 0 | 0 0 | 4 0 | 4 0 | 2 0 | 0 0 | 1 0 | 0 0 | 0 0 | 1 0 | 1 0 | 2 0 | 1 0 | 2 0 | 2 0 | 1 0 | 1 1 | 0 0 | 1 0 | 1 0 | 1 0 |

The preceding results of the greenhouse tests are indicative of the principal phytotoxic properties of the compounds of this invention. It will be understood that when the compounds are employed outdoors under uncontrolled conditions of climate and plant growth, the application rates must be adjusted. More active agent will be required where the weeds have been toughened by adverse growing conditions, or where the application method is inefficient or wasteful. It is customary in the art to make suitable adjustments of application rate to compensate for the conditions which are not present in well-controlled greenhouse tests. An application rate of at least twice the rate employed in the greenhouse is usual.

The new herbicides disclosed herein are particularly useful in post-emergent control of broadleaf weeds in peanuts, corn and small grains. Those which are more effective as pre-emergent herbicides may be used to combat both broadleaf weeds and grasses, particularly in corn, grain sorghum, rice, wheat and in some instances, also in cotton and soybeans. Compounds which are obtainable as oils, rather than high melting solids are more easily formulated and are preferred for use in combinations with other herbicides so as to obtain more desirable selectivity of control of unwanted vegetation.

We claim:

1. A selective herbicidal compound having the structural formula

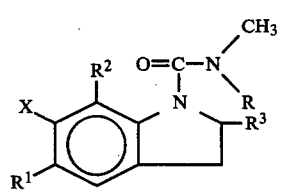

in which R, $R^2$, $R^3$ and X are hydrogen and $R^1$ is N,N-dimethylsulfamyl.

2. A selective herbicidal compound having the structural formula

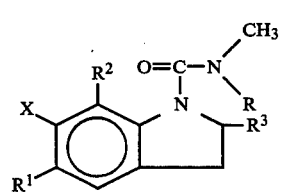

in which R, $R^2$, and $R^3$ and X are hydrogen and $R^1$ is N,N-diethylsulfamyl.

3. A selective herbicidal compound having the structural formula

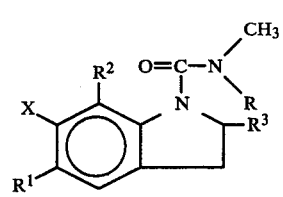

in which R, $R^2$, and $R^3$ and X are hydrogen and $R^1$ is N-methoxy-N-methylsulfamyl.

4. A selective herbicidal compound having the structural formula

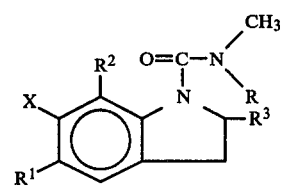

in which R is methyl, $R^1$ is bromo, $R^2$ is N,N-dimethylsulfamyl and $R^3$ and X are hydrogen.

5. A selective herbicidal compound having the structural formula

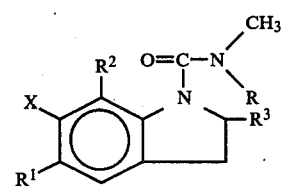

in which R, $R^3$ and X are hydrogen, $R^1$ is bromo and $R^2$ is N,N-dimethylsulfamyl.

6. A selective herbicidal compound having the structural formula

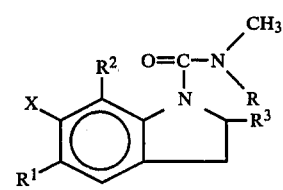

in which R is methyl, $R^1$ is N,N-dimethylsulfamyl and $R^2$, $R^3$ and X are hydrogen.

7. A selective herbicidal compound having the structural formula

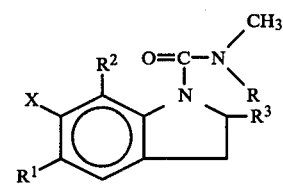

in which R is methyl, $R^1$ is N,N-diethylsulfamyl and $R^2$, $R^3$ and X are hydrogen.

8. A selective herbicidal compound having the structural formula

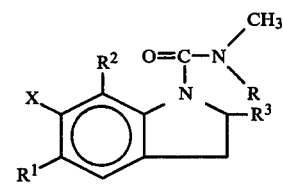

in which R is methyl, $R^1$ is N-methoxy-N-methylsulfamyl and $R^2$, $R^3$ and X are hydrogen.

* * * * *